US 9,717,619 B2

(12) United States Patent
Dodin (10) Patent No.: US 9,717,619 B2
(45) Date of Patent: Aug. 1, 2017

(54) ANKLE STABILIZATION/SPRAIN PREVENTION IN A SHOE (75) Inventor: Boris Dodin, Glun (FR)

(73) Assignee: Honeywell International Inc., Morris Plains, NJ (US)

(*) Notice: Subject to any disclaimer, the term of this patent is extended or adjusted under 35 U.S.C. 154(b) by 244 days.

(21) Appl. No.: 14/352,567

(22) PCT Filed: Nov. 1, 2011

(86) PCT No.: PCT/US2011/058698
§ 371 (c)(1),
(2), (4) Date: Apr. 17, 2014

(87) PCT Pub. No.: WO2013/066313
PCT Pub. Date: May 10, 2013

(65) Prior Publication Data
US 2014/0243724 A1 Aug. 28, 2014

(51) Int. Cl.
A61F 5/01 (2006.01)
A43B 7/20 (2006.01)
A43B 7/24 (2006.01)

(52) U.S. Cl.
CPC .............. *A61F 5/0102* (2013.01); *A43B 7/20* (2013.01); *A43B 7/24* (2013.01); *A61F 5/0127* (2013.01); *A61F 5/0111* (2013.01)

(58) Field of Classification Search
CPC .. A61F 5/00; A61F 5/01; A61F 5/0102; A61F 5/0127; A43B 7/14; A43B 7/18; A43B 7/20; A43B 5/04; A43B 5/1625; A43B 5/1691
USPC ........... 602/27, 65; 36/89, 118.2, 115, 118.3, 36/118.8
See application file for complete search history.

(56) References Cited

U.S. PATENT DOCUMENTS

| 1,205,206 A | 11/1916 | Hofmeister |
| 1,549,382 A | 8/1925 | Riddell |
| 3,584,622 A | 6/1971 | Domenico |

(Continued)

FOREIGN PATENT DOCUMENTS

| EP | 0752820 A1 | 1/1997 |
| WO | 2007098898 A3 | 9/2007 |
| WO | 2010065097 A1 | 6/2010 |

OTHER PUBLICATIONS

Forestier et al.; "The Effects of an Ankle Destabilization Device on Muscular Activity while Walking"; Int J Sports Med, pp. 1-7, dated Aug. 4, 2004.

(Continued)

*Primary Examiner* — Keri J Nelson
(74) *Attorney, Agent, or Firm* — Conley Rose, P.C.; Kristin Jordan Harkins (57) ABSTRACT Embodiments relate to shoes with ankle support elements, typically including a foot support element and a leg support element which are joined together via a joint to allow the leg support element to pivot with respect to the foot support element. The joint is typically located behind the ankle bone and at a height at least as great as the ankle bone. Straps are typically used to tighten the support elements for a good fit. Embodiments typically are formed so that neither the support elements nor the straps contact the ankle bone. And typically the foot and leg support elements work together to limit supination and adduction, while allowing fairly free extension.

19 Claims, 4 Drawing Sheets

(56) References Cited

U.S. PATENT DOCUMENTS

| | | | |
|---|---|---|---|
| 4,313,433 A | 2/1982 | Cramer | |
| 4,367,733 A | 1/1983 | Stromgren | |
| 4,517,968 A | 5/1985 | Greene et al. | |
| 4,727,863 A | 3/1988 | Nelson | |
| 4,776,111 A * | 10/1988 | Crowley | A43B 5/00 |
| | | | 36/114 |
| 4,875,476 A | 10/1989 | Garcia | |
| 5,069,202 A | 12/1991 | Prock | |
| 5,109,613 A | 5/1992 | Van Dyke | |
| 5,199,941 A | 4/1993 | Makinen | |
| 5,217,431 A | 6/1993 | Toronto et al. | |
| 5,486,157 A | 1/1996 | DiBenedetto | |
| 5,496,263 A | 3/1996 | Fuller, II et al. | |
| 5,678,330 A | 10/1997 | Van Dyke et al. | |
| 5,778,563 A | 7/1998 | Ahlbaeumer | |
| 5,795,316 A | 8/1998 | Gaylord | |
| 6,053,884 A | 4/2000 | Peters | |
| 6,299,587 B1 | 10/2001 | Birmingham | |
| 6,557,271 B1 | 5/2003 | Weaver, III | |
| 6,775,929 B2 | 8/2004 | Katz et al. | |
| 7,171,766 B2 | 2/2007 | Bouche et al. | |
| 7,429,254 B1 * | 9/2008 | Engelman | A61F 13/06 |
| | | | 602/16 |
| 7,713,224 B1 | 5/2010 | Peters et al. | |
| 2005/0178028 A1 | 8/2005 | Light | |
| 2007/0213649 A1 | 9/2007 | Gaylord et al. | |
| 2008/0082034 A1 | 4/2008 | Wilkerson | |
| 2011/0066095 A1 * | 3/2011 | Price | A61F 5/0106 |
| | | | 602/16 |
| 2011/0308110 A1 * | 12/2011 | Berns | A43B 3/0063 |
| | | | 36/89 |

OTHER PUBLICATIONS

PCT/US2011/058698, PCT International Search Report, dated Jul. 4, 2012, 4 pages.

PCT/US2011/058698, PCT Written Opinion of the International Searching Authority, dated Jul. 4, 2012, 7 pages.

European Patent Application No. 11779948.6, Examination Report, dated Mar. 9, 2017, 4 pages.

\* cited by examiner

ANKLE STABILIZATION/SPRAIN PREVENTION IN A SHOE

CROSS-REFERENCE TO RELATED APPLICATIONS

This application is related to and claims priority to PCT International Application No. PCT/US2011/058698 entitled "Ankle Stabilization/Sprain Prevention in a Shoe" and filed on Nov. 1, 2011 which is assigned to the Assignee of the present application and hereby incorporated by reference as if reproduced in its entirety.

STATEMENT REGARDING FEDERALLY SPONSORED RESEARCH OR DEVELOPMENT

Not applicable.

REFERENCE TO A MICROFICHE APPENDIX

Not applicable.

FIELD

Embodiments relate generally to ankle stabilization, and more specifically to a device for use with a shoe for minimizing the likelihood and/or severity of ankle sprain injuries.

BACKGROUND

A sprained ankle can be quite painful and can vastly limit mobility. Ankle sprains may occur anytime someone is on their feet, either walking or running, for example. Thus, ankle sprains may occur during leisure time activities, during work, or when simply out and about town. Many ankle sprains occur during work, and often ankle sprains can sufficiently disable the person so that they must miss work for a significant period of time (for example, 8 days to 45 days, depending upon the severity of the sprain). Embodiments disclosed herein are designed to stabilize the user's ankle, in order to minimize the risk and/or severity of an ankle sprain.

SUMMARY

Aspects of the disclosed embodiments may relate to an ankle stabilization device for use with a shoe having a sole, an exterior with two sides, a length, a heel, and an ankle bone portion, comprising one or more of the following features and/or functions: a foot support element; a leg support element; an articulation joint attaching the leg support element to the foot support element and allowing free extension movement; and a plurality of means for tightening the foot and leg support elements for a close fit; and wherein: the foot support element has at least one tightening means attached, and the leg support element has at least one tightening means attached; and the joint is positioned to the rear of the ankle bone portion of the shoe and at a height at least as great as the ankle bone support portion of the shoe. In some embodiments, the assembly of the foot support element and the leg support element may be sufficiently rigid to prevent more than about 40 degrees combined supination and adduction in about 30 ms. In some embodiments, an assembly of the foot support element and the leg support element may provide an average resistive force of about 15 N-m or greater for combined supination and adduction. In some embodiments, the foot support element, the leg support element, the joint and the straps do not contact the ankle bone portion of the shoe. In some embodiments, the foot support element may extend forward from the heel of the shoe on both sides of the shoe for at least ⅓ the length of the shoe, or alternatively to about the arch of the shoe. In some embodiments, the foot and/or leg support elements may be formed of TPU. In some embodiments, the foot support element may be securely fixed to the exterior of the shoe. In some embodiments, the foot support element may comprise a horizontal centerline and raised portions located approximately along the horizontal centerline; and/or the leg support element may comprise a vertical centerline and raised portions located along the vertical centerline.

In other aspects, disclosed embodiments may relate to an ankle stabilization device comprising one or more of the following features and/or functions: a shoe comprising a sole, an exterior having two sides, a length, a rear including a heel, (an arch), and an ankle bone portion; a foot support element attached to the exterior of the shoe; a leg support element; an articulation joint attaching the leg support element to the foot support element and allowing free extension movement; and a plurality of non-elastic straps; wherein: the foot support element has at least one strap attached, and the leg support element has at least one strap attached; an assembly of the foot support element and the leg support element is sufficiently rigid to prevent more than 40 degrees combined supination and adduction in about 30 ms and/or to provide an average resistive force of about 15 N-m or greater for combined supination and adduction; and the joint is positioned to the rear of the ankle bone portion of the shoe and at a height at least as great as the ankle bone portion of the shoe. In some embodiments, the range of combined supination and adduction allowed by the assembly of the foot and leg support elements may range from about 25 degrees to about 40 degrees. In some embodiments, the articulation joint may comprise two hinge joints located on each side of the shoe. In some embodiments, the foot support element, the leg support element, and the straps may not contact the ankle bone portion of the shoe.

BRIEF DESCRIPTION OF THE DRAWINGS

For a more complete understanding of the present disclosure, and for further details and advantages thereof, reference is now made to the accompanying drawings, in which.

DETAILED DESCRIPTION

The following brief definition of terms shall apply throughout the application:

The term "shoe" means a shoe, boot, or other type of footwear for a human being;

The term "ankle bone" means the bony protrusions on either side of a human ankle, and may include the medial and/or lateral malleolus for example;

The term "comprising" means including but not limited to, and should be interpreted in the manner it is typically used in the patent context;

The phrases "in one embodiment," "according to one embodiment," and the like generally mean that the particular feature, structure, or characteristic following the phrase may be included in at least one embodiment of the present invention, and may be included in more than one embodiment of the present invention (importantly, such phrases do not necessarily refer to the same embodiment);

If the specification describes something as "exemplary" or an "example," it should be understood that refers to a non-exclusive example;

The terms "about" or approximately" or the like, when used with a number, may mean that specific number, or alternatively, a range in proximity to the specific number, as understood by persons of skill in the art field; and If the specification states a component or feature "may," "can," "could," "should," "preferably," "possibly," "typically," "optionally," "for example," or "might" (or other such language) be included or have a characteristic, that particular component or feature is not required to be included or to have the characteristic. Such component or feature may be optionally included in some embodiments, or it may be excluded.

Figure 1:
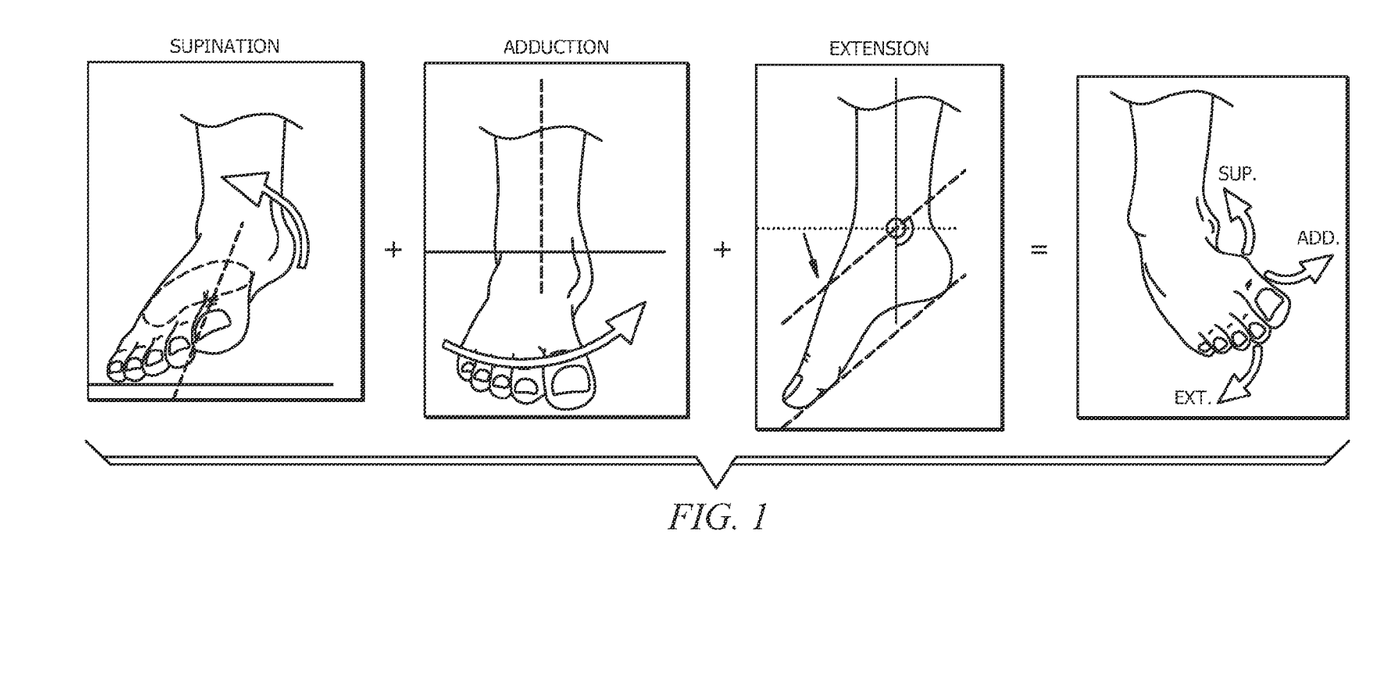
FIG. 1 provides an illustrative example of the three different types of movement which may possibly be experienced by the human foot during unrestrained ambulation.

Ankle sprains typically occur if the foot rapidly experiences large movement in more than one direction. A typical human foot/ankle generally has three different movement modes: supination/pronation, adduction/abduction, and extension/flexion. FIG. 1 illustrates these different movement modes. So, rapid and/or large foot/ankle movement in two or more of these movement modes is likely to produce an ankle sprain (depending of course on the strength and flexibility of the specific person's ankle, for example). Disclosed embodiments attempt to minimize the risk and/or severity of an ankle sprain by limiting two of the three movement modes, slowing down the movement and/or limiting the range of movement for these two movement modes. Typically, the extension movement should be substantially free of restriction, in order for the person to ambulate effectively (since walking, for example, requires extension at a minimum). Thus, embodiments typically act to limit supination and adduction (for example, acting as a brake to reduce the speed at which the user's foot can move in these directions), while allowing free extension without limitation (although it might also be possible to limit extension slightly).

Supination and adduction are typically limited in disclosed embodiments by using a support device with two fairly rigid elements. The elements should be sufficiently rigid to limit foot movement as necessary to minimize the type of foot/ankle movement that would result in a sprain, but cannot be too rigid or else they would restrict the user's gait too much, leading to stress on other joints (like the user's knee, for example). In some embodiments, the elements would jointly provide an average resistance force against combined supination and adduction of movement equal to or greater than about 15 N-m. In other embodiments, each element would provide an average resistance force against the corresponding type of movement (such as supination or adduction, for example) equal to or greater than 15 N-m. One element is typically located along the foot, while the other element typically extends up towards the leg (such that the two elements together form an L-like shape).

When used together, the elements act to limit supination and adduction (restricting movement of the foot/ankle in these two directions in a way to minimize the chances of an ankle sprain). And typically, the two elements are linked together by a joint that allows free movement of the foot in the extension direction. In some embodiments, the elements seek to limit the combination of supination and adduction movement so that the total (combined supination and adduction movement) is less than about 40 degrees in a 30 second timeframe. In some embodiments, eversion may be limited by the elements to less than about 40 degrees in 30 seconds. In other embodiments, the angle of movement might be limited to less than about 40 degrees in a 60 ms timeframe, or alternatively in a timeframe ranging from 35 ms to 120 ms. The angle of movement in some embodiments might exceed about 40 degrees if the movement can be delayed or slowed sufficiently so that it takes place in more than about 120 ms.

Typical embodiments incorporate the two support elements and joint into a shoe or boot design (although in other embodiments it might be possible to have a separate or removable support device that could be fitted over the user's show or boot). Typically, the foot support element would be firmly (typically permanently) affixed to the shoe (typically the exterior of the shoe), and the leg support element would be attached to the foot support element by the joint (such that the foot support element could pivot freely with respect to the leg support element in the extension direction). Two or more straps (or some other attachment means) would typically be used to fit the support elements closely to the user's foot. The straps typically are non-elastic, allowing for the user to obtain a close fit that will keep the support elements properly positioned on the shoe and user's foot during ambulation. Typically, one strap would span the top of the user's shoe or foot, while the second strap would span the upper portion of the shoe associated with the lower part of the user's leg (i.e. the upper ankle area, above the point where the leg connects to the upper foot).

Figure 2:
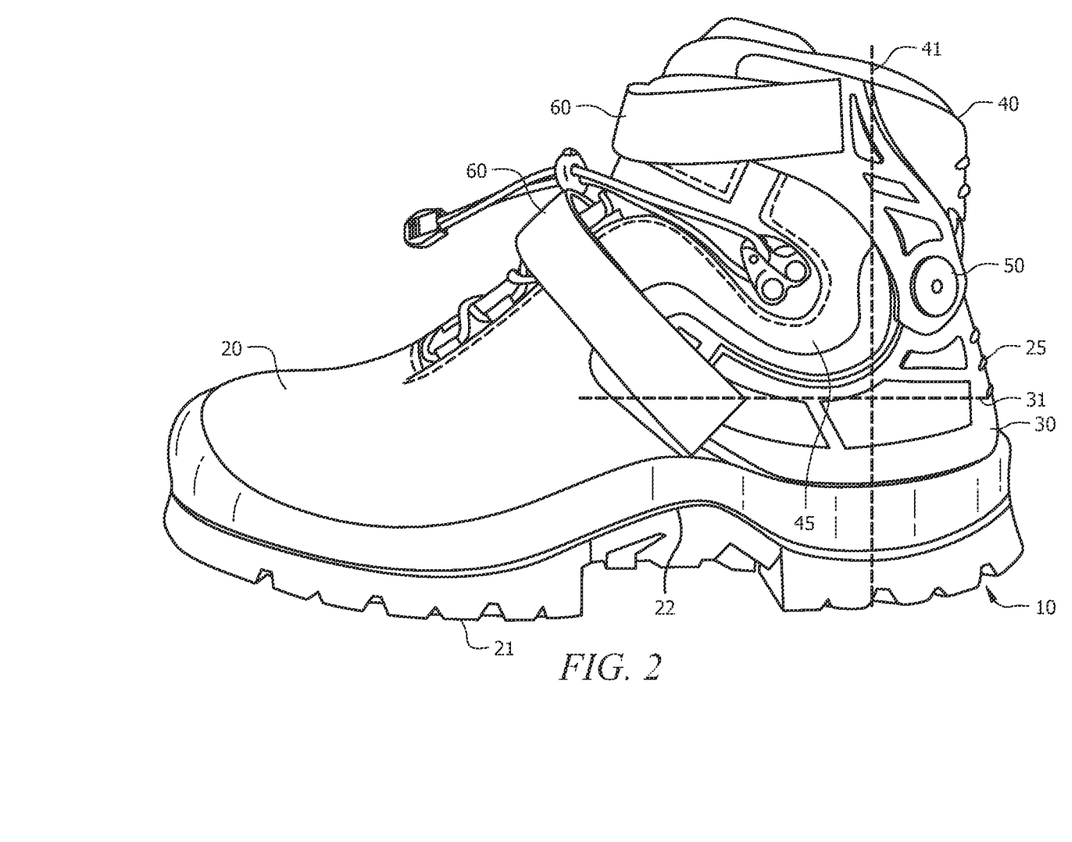
FIG. 2 illustrates an exemplary embodiment of an ankle stabilization device with a lateral foot support element and a vertical leg support element attached to the exterior of a shoe.

FIG. 2 illustrates an embodiment of an ankle stabilization device 10. The ankle stabilization device 10 of FIG. 2 includes a shoe 20, a lateral foot support element 30, a vertical leg support element 40, a joint 50, and two straps 60. The support elements of FIG. 2 are firmly attached to the exterior of the shoe 20, forming an integrated device. More specifically, in FIG. 2 the foot support element 30 is firmly attached to the exterior of the shoe 20, and the leg support element 40 is attached to the foot support element 30 by joint 50. Joint 50 of FIG. 2 is designed to allow free motion between the leg support element 40 and the foot support element 30 in the extension direction. In FIG. 2, joint 50 comprises two hinge joints connecting the leg support element 40 to the foot support element 30 on both sides of the shoe (typically in mirror or symmetrical fashion, such that the hinge joints are aligned on either side of the shoe), allowing free rotation of the leg support element 40 with respect to the foot support element 30 in a single direction (typically extension). In FIG. 2, one strap 60 is attached to the foot support element 30 (allowing the foot support element 30 to be secured in place on the user's foot), and a second strap 60 is attached to the leg support element 40 (allowing the leg support element 40 to be firmly secured to the user's ankle). And in the embodiment of FIG. 2, the ankle bone 45 portion of the shoe (i.e. the portion of the shoe designed to fit over and cover the user's ankle bone) would not be contacted and/or covered by the support elements 30, 40 or the straps 60.

The foot support element 30 of FIG. 2 extends forward from the heel 25 of the shoe on both sides of the shoe 20. Thus, the foot support element 30 of FIG. 2 enwraps the back of the heel 25 of the shoe and extends forward from the heel 25 along at least the base of the shoe (for example, along the lower portion of the upper of the shoe, above the sole 21). In some other embodiments, the foot support element 30 might instead comprise two separate elements, one for each side of the shoe, and may not fully enwrap the heel 25; but in the embodiment of FIG. 2, the foot support element 30 is a single, integrated unit that provides support on both sides of the shoe 20. In FIG. 2, the foot support element 30 may be symmetrical about the centerline of the shoe, so that it is the same on both sides of the shoe. In the embodiment of FIG. 2, the foot support element 30 does not extend over any portion of the sole 21, but merely lies on the lateral side of the shoe (although it may be possible that other embodiments could have a portion of the foot support element 30 that includes a sole portion). So the foot support element 30 of the embodiment of FIG. 2 does not include any additional support for the sole or bottom of the shoe or foot. The foot support element 30 may extend forward to approximately the arch 22 of the shoe. Alternatively, the foot support element 30 may extend forward for at least about ⅓ of the shoe's length. Regardless, the foot support element typically would not extend so far forward that it would interfere with the ability of the shoe to bend at the toe box (as this might interfere with an effective walking motion).

In FIG. 2, the foot support element 30 may extend upward on the rear/heel portion to allow for the joint 50 connection with the leg support element 40, may extend upward (typically at an angle of about 30-60 degrees, and in FIG. 2 at an angle of about 45 degrees) near the arch of the shoe and/or the front portion of the foot support element (providing a point of attachment for the strap 60 and allowing for the strap 60 to extend out at an angle to comfortably span the top of the shoe), and/or may be lower (scooping downward, for example) in the center portion of the support and/or the portion of the support located in proximity to the ankle bone 45 portion of the shoe 20. So while portions of the foot support element 30 may extend upward to the height of the ankle bone, the portion of the foot support in proximity to the ankle bone 45 would be lower (so that the foot support element would not contact the ankle bone). In other words, the shape of the foot support element 30 provides clearance of the ankle bone 45. The bottom edge of the foot support element of FIG. 2 typically is shaped so that it matches the curvature of the upper edge of the sole of the shoe 20, with the foot support element 30 typically being located on the lower portion of the shoe's upper so that the foot support element's lower edge abuts or otherwise interfaces with the upper edge of the shoe's sole. And in FIG. 2, the foot support element 30 may have one or more raised sections located approximately along the centerline of the support element, in which the raised portion of the support element has greater thickness than the remaining portions of the support element. This may have the result of acting as if there is a ridge in the center of the foot support element 30, such that the foot support element 30 of FIG. 2 may be more rigid near its center and more flexible towards its edges.

The leg support element 40 of FIG. 2 (typically located primarily near the rear of the shoe) extends upward on both sides of the shoe 20 from the joint 50 connection with the foot support element 30 to a location above the ankle bone 45 portion of the shoe. In the embodiment of FIG. 2, the leg support element 40 comprises two vertical side elements (typically located approximately at the rear of the shoe, with one side element on each side of the shoe) and a connecting rear element that encircles the rear of the shoe to join the elements into a single integrated leg support element 40. In some embodiments, however, the leg support element 40 might instead comprise two separate elements, one for each side of the shoe, and might only be connected by the joint 50 and the strap(s) 60. In FIG. 2, the leg support element 40 may be symmetrical about the centerline of the shoe. In the integrated leg support element of FIG. 2, the connecting rear element is typically located towards the top of the leg support element 40, and typically does not extend all the way down to the joint 50 area. In other words, there is typically a gap on the back of the shoe between the foot support element 30 and the leg support element 40 near the joint 50 connection (and this gap may allow sufficient space for the leg support element 40 to pivot with respect to the foot support element 30 during ambulation without the two elements contacting, for example, so that the joint 25 can effectively provide free motion throughout the range necessary for ambulation). Alternatively, this gap could be covered by an elastic material that would allow the range of motion during ambulation.

In the embodiment of FIG. 2, the upper portion of the leg support element 40 extends forward, partially encircling the upper ankle of the shoe 20. The strap 60 typically is anchored to this portion, allowing the strap 60 to work with the leg support element 40 to encircle the upper ankle of the shoe 20 during usage to securely fit the leg support element 40 to the shoe and/or user's foot. The shape of the leg support element of FIG. 2 provides clearance of the ankle bone 45 portion of the shoe. So In FIG. 2, the leg support element may extend upward at an angle or arc from the joint 50 (on both sides of the shoe 20), which is typically located rearward (behind) the ankle bone 45 portion of the shoe, and then perhaps extend forward and/or backward horizontally. And in FIG. 2, the leg support element 40 may have one or more raised sections located approximately along the vertical centerline of the support element, in which the raised portion of the support element has greater thickness than the remaining portions of the support element. This may have the result of acting as if there is a ridge in the center of the leg support element 40, such that the leg support element 40 may be more rigid near its center and more flexible towards its edges.

The assembly of the foot support element 30 and the leg support element 40 (which may also include the joint 50) of FIG. 2 is sufficiently rigid to minimize adduction and supination motion during use of the device to a level that is unlikely to result in a sprain, but is not so rigid as to completely prevent adduction and supination (since this might place strain on the user's other joints, such as the knee, and could possibly result in injury). In some embodiments, the assembly may limit the combined supination and adduction motions to less than about 40 degrees in about 30 seconds, but may also have sufficient flexibility to allow at least 25 degrees of flexing. In some embodiments, the assembly may allow a range of combined supination and adduction motion between about 25-40 degrees in a timeframe of about 30 seconds. In FIG. 2, the foot and leg support elements may have a hardness of about 100 shores. The foot and leg support elements of FIG. 2 may also have a thickness of about 1.5 mm. In FIG. 2, the foot and/or leg support elements may be made of TPU (such as thermoplastic polyurethane, for example).

The leg support element 40 of FIG. 2 is joined to the foot support element 30 by a joint 50. More specifically, two pivoting hinge joints 50 connect the leg support element 40 to the foot support element 30, with one hinge on either side of the shoe 20. This pivot connection allows the leg support element 40 to pivot freely in the extension direction during ambulation (such that the device 10 does not restrict extension of the user's foot during ambulation), and may allow the leg support element 40 and the foot support element 30 to work together to effectively limit movement in the supination and adduction directions (to minimize the chances of a sprain during ambulation by restricting the speed or amount of movement in those directions). The joint 50 of FIG. 2 may be located (on both sides of the shoe) to the rear (behind) the ankle bone 45 portion of the shoe, typically at a level (height) equal to or higher (above) than the ankle bone 45 portion of the shoe. Typically, the joint 50 of FIG. 2 may be located at about the rear of the shoe at a height approximately equal to that of the ankle bone 45 portion of the shoe. This position of the joint may tend to provide effective extension movement for ambulation without significant discomfort. And typically, when the leg support element 40 and the foot support element 30 are linked by the joint 50, no part of the integrated support element contacts or covers (extends over) the ankle bone 45 portion of the shoe. Rather, an opening exists on each side of the device 10 corresponding to the ankle bone 45 portion of the shoe (so that the integrated support element (for example, the assembly of foot and leg elements) may encircle the ankle bone 45 portion of the shoe, but will not typically contact and/or cover it).

While embodiments may use various types of securing means to securely fit the foot and leg support elements 30, 40 in place during usage (ambulation), in FIG. 2 a plurality of straps 60 may be used to securely fix the device 10 (typically with at least one strap for the foot support element 30 and at least one strap for the leg support element, respectively). In FIG. 2, typically one strap 60 may be used to link the two sides of the foot support element 30 (typically near the front of the foot support element) by spanning the top of the shoe 20, and one strap 60 may be used to link the two sides of the leg support element 40 (typically near the front top of the leg support element) by spanning the front of the upper ankle of the shoe 20. The plurality of straps may each be firmly attached to one side of the support element and have at least sufficient length to span the shoe to connect to the corresponding location on the other side of the respective support element. The straps 60 may each comprise a fastening means, such as Velcro™ hook and loop connectors, buckles, snaps, etc. The straps 60 are typically non-elastic, to allow for a secure fit that does not change during ambulation. By way of example, the straps 60 of FIG. 2 might be made of polypropylene. And the straps 60 of FIG. 2 are placed/configured so that they do not contact and/or cover the ankle bone 45 portion of the shoe when in use.

Figure 3:
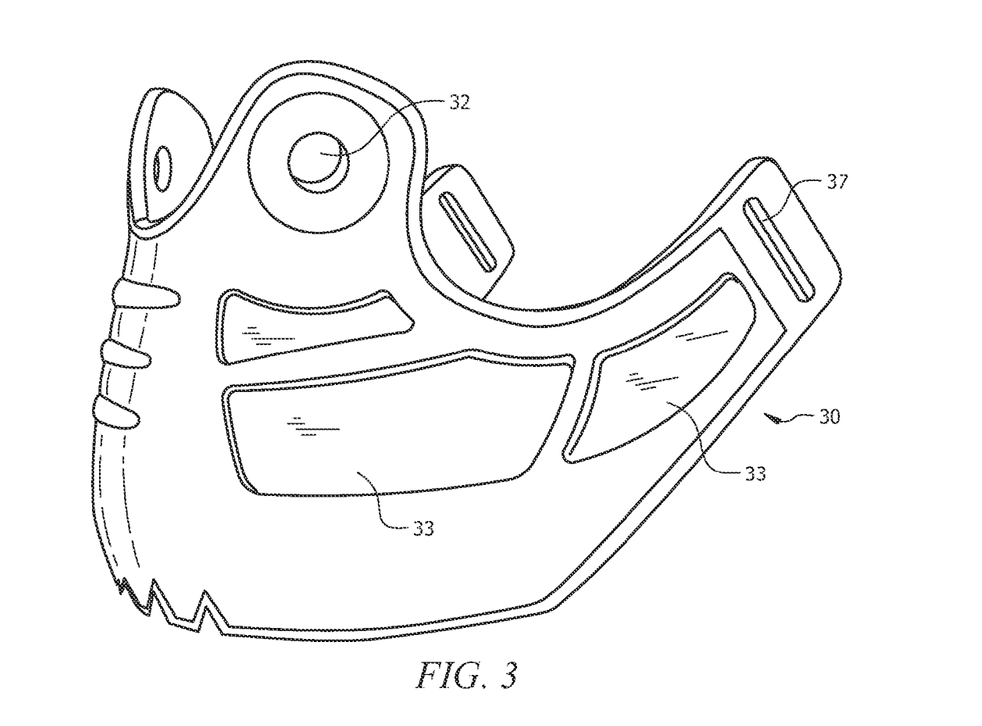
FIG. 3 illustrates an exemplary embodiment of a lateral foot support element.
Figure 4:
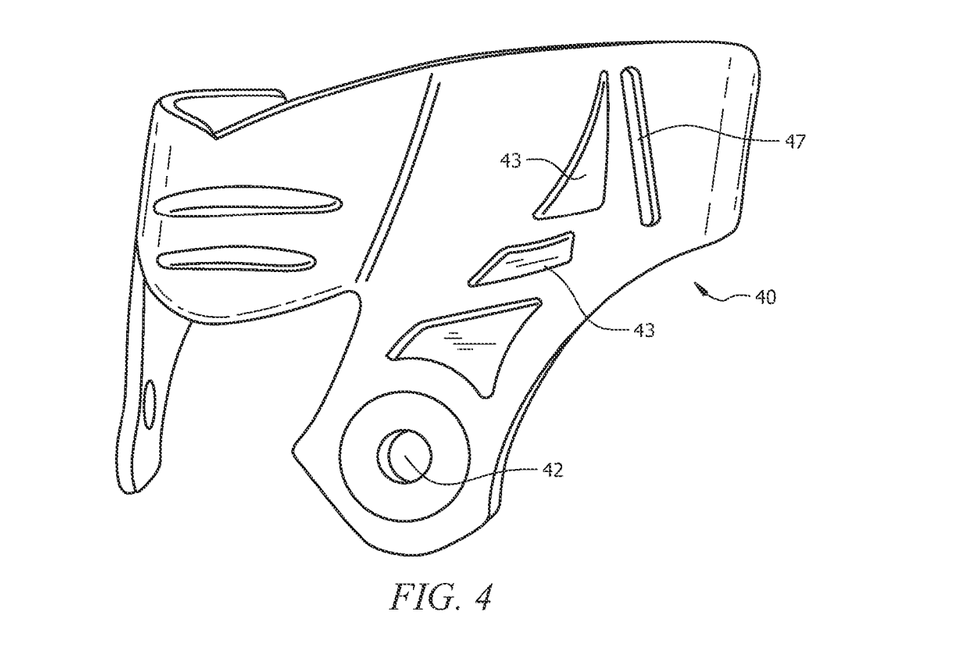
FIG. 4 illustrates an exemplary embodiment of a vertical leg support element.

FIG. 3 illustrates an embodiment of the foot support element 30. The foot support element 30 of FIG. 3 includes a pair of holes 32 designed to match corresponding holes in the leg support element 40 to form the joint 50, and a pair of slots 37 designed to accept a strap 60 extending from one slot to the other in order to tightly fit the foot support element 30 to the shoe and/or user's foot (so that it can provide effective support). The foot support element 30 of FIG. 3 may also be shaped so that its bottom edge will fit snuggly atop the sole of the shoe 20. Furthermore, the foot support element of FIG. 3 has a plurality of raised portions on its exterior surface (such that those raised portions of the element have greater thickness and rigidity). FIG. 4 illustrates an embodiment of the leg support element 40. The leg support element of FIG. 4 includes a pair of holes 42 designed to match corresponding holes in the foot support element 30 to form the joint 50, and a pair of slots 47 designed to accept a strap 60 extending from one slot to the other in order to tightly fit the leg support element 40 to the shoe and/or user's ankle. And, the leg support element of FIG. 4 has a plurality of raised portions on its exterior surface (such that those raised portions of the element have greater thickness and rigidity). The raised portions 33 in the foot support element 30 in the embodiment of FIG. 3 and the raised portions 43 in the leg support element 40 in the embodiment of FIG. 4 are typically located to provide additional support along the vertical and horizontal support axis (for example, the two support axis 31 and 41, as shown in FIG. 2). Thus, the raised portions for each support element are typically located approximately along the centerline of each support element on both sides of the shoe 20.

Figure 5:
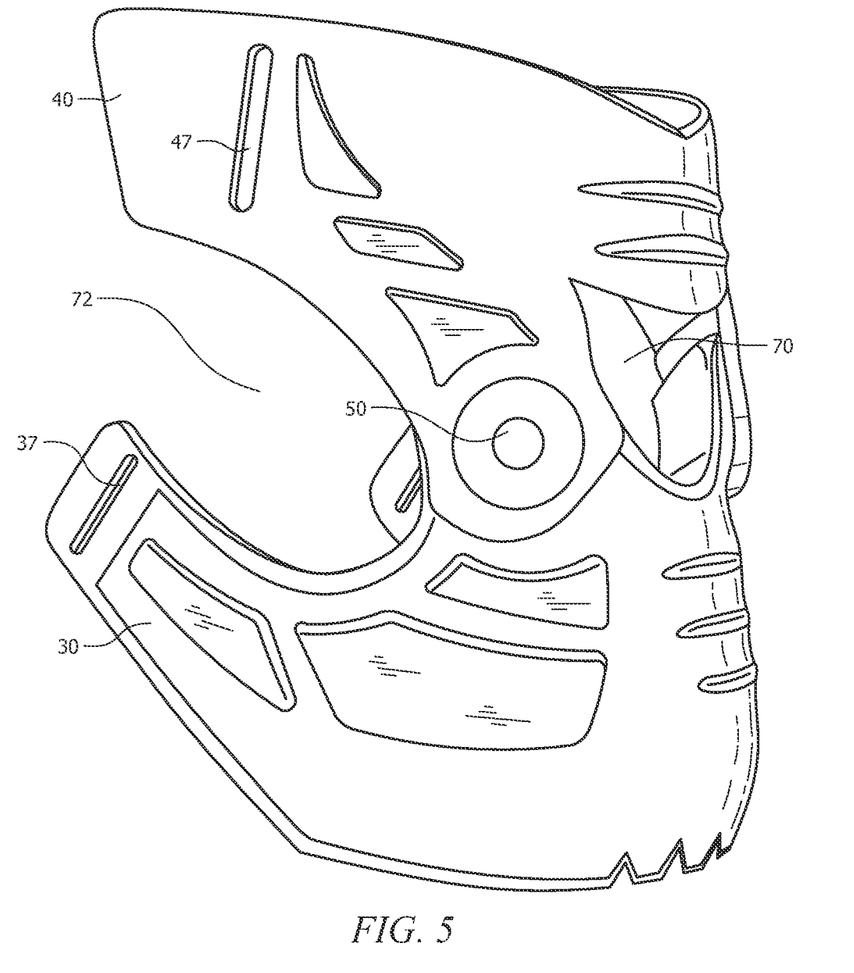
FIG. 5 illustrates an exemplary embodiment of the support elements of FIG. 3 and FIG. 4 aligned to form a joint.

FIG. 5 illustrates the combined assembly of the support elements. FIG. 5 shows the relative position of the leg support element 40 with respect to the foot support element 30, and shows that in practice the holes 32 in the foot support element are aligned with the holes 42 in the leg support element to form joint 50. Typically, the joint would be completed by having a hinge pin inserted into each of the holes of the joint 50. FIG. 5 also shows how the elements are shaped so that there is a gap 70 formed between the rear portion of the leg support element 40 and the rear portion of the foot support element 30 to assist in free motion about the joint 50. And FIG. 5 also shows how the elements are shaped so that there is an opening 72 so that the support elements will not contact or cover the ankle bone 45 portion of the shoe. The support elements of FIG. 5 may be mirror images about the centerline (medial) plane of the foot/ankle/shoe. In the embodiments of FIGS. 3 and 4, both the foot support element 30 and the leg support element 40 are formed to be symmetrical about their centerline plane (so that each side is a mirror image of the other). In other embodiments, however, each side of the support elements may differ somewhat in shape for design purposes, depending for example on the specific shape of the shoe 20.

Typically, the device 10 of FIG. 2 might be formed by providing a shoe, providing or forming the foot and leg support elements, securely attaching the foot support element to the exterior of the shoe, attaching the leg support element to the foot support element via the joint, and affixing the straps to the support elements. Attaching the foot support element to the shoe may include positioning the foot support element along the upper edge of the sole of the shoe and/or positioning the foot support element to enwrap the heel of the shoe. Attaching the leg support element to the foot support element may include aligning matching holes in the foot and leg support elements and inserting a hinge pin through each hole. Forming the foot and leg support elements may include molding the support elements, which may include pouring flowable material into a mold, closing the mold, and ejecting the solidified element from the mold. The foot support element may be affixed to the shoe by stitching, adhesive, and/or other attachment means.

And in use, the shoe 20 might be worn on the user's foot in typical fashion. Once the shoe 20 is pulled onto the user's foot and the laces or other fastening means are used to tighten the shoe 20 in place on the user's foot, the user may then use the strap(s) 60 to provide a tight fit of the support elements. Typically, the user might tighten the straps more when uneven terrain is anticipated. The user may then ambulate (walk, etc.) in normal fashion, and the device 10 of FIG. 2 may provide additional ankle support to minimize the risk of an ankle sprain. During ambulation, the device 10 may provide free motion in the extension direction, while restricting motion in the supination and adduction directions. And as noted above, the support elements may be sufficiently rigid to limit foot motion in supination and adduction directions to less than about 40 degrees combined or total movement, but may not be completely rigid (allowing at least about 25 degrees combined or total flexing so as not to put excess strain on the user's other joints, such as the knee joint).

While various embodiments in accordance with the principles disclosed herein have been shown and described above, modifications thereof may be made by one skilled in the art without departing from the spirit and the teachings of the disclosure. The embodiments described herein are representative only and are not intended to be limiting. Many variations, combinations, and modifications are possible and are within the scope of the disclosure. Alternative embodiments that result from combining, integrating, and/or omitting features of the embodiment(s) are also within the scope of the disclosure. Accordingly, the scope of protection is not limited by the description set out above, but is defined by the claims which follow, that scope including all equivalents of the subject matter of the claims. Each and every claim is incorporated as further disclosure into the specification and the claims are embodiment(s) of the present invention(s). Furthermore, any advantages and features described above may relate to specific embodiments, but shall not limit the application of such issued claims to processes and structures accomplishing any or all of the above advantages or having any or all of the above features.

Additionally, the section headings used herein are provided for consistency with the suggestions under 37 C.F.R. 1.77 or to otherwise provide organizational cues. These headings shall not limit or characterize the invention(s) set out in any claims that may issue from this disclosure. Specifically and by way of example, although the headings might refer to a "Field," the claims should not be limited by the language chosen under this heading to describe the so-called field. Further, a description of a technology in the "Background" is not to be construed as an admission that certain technology is prior art to any invention(s) in this disclosure. Neither is the "Summary" to be considered as a limiting characterization of the invention(s) set forth in issued claims. Furthermore, any reference in this disclosure to "invention" in the singular should not be used to argue that there is only a single point of novelty in this disclosure. Multiple inventions may be set forth according to the limitations of the multiple claims issuing from this disclosure, and such claims accordingly define the invention(s), and their equivalents, that are protected thereby. In all instances, the scope of the claims shall be considered on their own merits in light of this disclosure, but should not be constrained by the headings set forth herein.

Use of broader terms such as comprises, includes, and having should be understood to provide support for narrower terms such as consisting of, consisting essentially of, and comprised substantially of Use of the term "optionally," "may," "might," "possibly," and the like with respect to any element of an embodiment means that the element is not required, or alternatively, the element is required, both alternatives being within the scope of the embodiment(s). Also, references to examples are merely provided for illustrative purposes, and are not intended to be exclusive.

What is claimed is:

1. An ankle stabilization device comprising:
   a shoe comprising a sole, an exterior having two sides, a length, a rear including a heel, and an ankle bone portion configured to cover an ankle bone of a user;
   a foot support element attached to the exterior of the shoe without covering the ankle bone portion of the shoe;
   a leg support element;
   an articulation joint attaching the leg support element to the foot support element in a configuration that forms an opening around the ankle hone portion of the shoe such that no part of the foot support element, the leg support element, and the articulation joint covers the ankle bone portion of the shoe, wherein the articulation joint allows free extension movement; and
   a plurality of non-elastic straps;
   wherein:
      the foot support element has at least one strap attached, and the leg support element has at least one strap attached without covering the ankle hone portion of the shoe;
      an assembly of the foot support element and the leg support element is sufficiently rigid to prevent more than 40 degrees combined supination and adduction within about 30 milliseconds (ms); and
      the articulation joint is positioned to the rear of the ankle bone portion of the shoe and at a height at least as great as the ankle hone portion of the shoe.

2. The device of claim 1 wherein the articulation joint comprises two hinge joints located on each side of the shoe.

3. The device of claim 2 wherein the foot support element extends forward from the heel of the shoe on both sides of the shoe for at least ⅓ the length of the shoe.

4. The device of claim 3 wherein the leg support element comprises vertical elements that extend upward from the joint on both sides of the shoe and a horizontal element that links the two vertical elements around the rear of the shoe.

5. The device of claim 1 wherein the foot support element, the leg support element, and the straps do not contact the ankle bone portion of the shoe.

6. An ankle stabilization device comprising:
   a shoe comprising a sole, an arch, two sides, a heel, and an ankle bone portion configured to cover an ankle bone;
   a foot support element attached to the shoe;
   a leg support element;
   a pair of hinge joints, with one hinge joint located on each side of the shoe and each hinge joint attaching the leg support element to the foot support element in a configuration that forms an opening around the ankle bone portion of the shoe such that no part of the foot support element, the leg support element, and the pair of hinge joints covers the ankle bone portion of the shoe, wherein each hinge joint allows free extension movement; and
   a plurality of non-elastic straps;
   wherein:
      the foot support element has at least one strap attached without covering the ankle bone portion of the shoe, and the leg support element has at least one strap attached without covering the ankle bone portion of the shoe;
      an assembly of the foot support element and the leg support element is sufficiently rigid to provide an average resistive force of about 15 N-m or greater for combined supination and adduction;

each of the foot support element, the leg support element, and the plurality of straps do not contact or cover the ankle bone portion of the shoe; and the pair of hinge joints does not contact the ankle bone portion of the shoe, and the pair of hinge joints are positioned to the rear of the ankle bone portion of the shoe and at a height at least as great as the ankle bone portion of the shoe.

7. The device of claim 6 wherein the foot support element extends forward from the heel of the shoe on both sides of the shoe to about the arch of the shoe.

8. The device of claim 6 wherein the foot support element and the leg support elements are formed of thermoplastic polyurethane (TPU).

9. The device of claim 6 wherein the foot support element is attached to the shoe by stitching and/or adhesive.

10. The device of claim 6 wherein the assembly of the foot support element, joints, and leg support element limit supination and adduction to prevent more than about 40 degrees combined supination and adduction in about 30 ms, but allow free extension movement during ambulation.

11. An ankle stabilization device configured for attachment to a shoe having a sole, an exterior with two sides, a length, a heel, and an ankle bone portion configured to cover an ankle bone of a user, the ankle stabilization device comprising:
    a foot support element;
    a leg support element;
    an articulation joint attaching the leg support element to the foot support element in a configuration that forms an opening around the ankle bone portion of the shoe such that no part of the foot support element, the leg support element, and the articulation joint covers the ankle bone portion of the shoe, wherein the articulation joint allows free extension movement; and
    a plurality of means for tightening the foot and leg support elements to the shoe;

wherein:
    the foot support element has at least one of the plurality of means for tightening attached without covering the ankle bone portion of the shoe, and the leg support element has at least one of the plurality of means for tightening attached without covering the ankle bone portion of the shoe; and
    the articulation joint is positioned to the rear of the ankle bone portion of the shoe and at a height at least as great as the ankle bone support portion of the shoe.

12. The device of claim 11 wherein the assembly of the foot support element and the leg support element is sufficiently rigid to prevent more than about 40 degrees combined supination and adduction in about 30 ms.

13. The device of claim 12 wherein the foot support element, the leg support element, the joint and the means for tightening do not contact the ankle bone portion of the shoe.

14. The device of claim 13 wherein an assembly of the foot support element and the leg support element provides an average resistive force of about 15 N-m or greater for combined supination and adduction.

15. The device of claim 13 wherein the foot support element extends forward from the heel of the shoe on both sides of the shoe for at least ⅓ the length of the shoe.

16. The device of claim 13 wherein the foot support element comprises a horizontal centerline and one or more raised portions located approximately along the horizontal centerline; and the leg support element comprises a vertical centerline and one or more raised portions located along the vertical centerline.

17. The device of claim 13 wherein the foot support element is securely fixed to the exterior of the shoe.

18. The device of claim 11 wherein the foot support element, the leg support element, and the means for tightening do not contact the ankle bone portion of the shoe.

19. The device of claim 11 wherein the foot support element and leg support element are formed of thermoplastic polyurethane (TPU).

* * * * *

UNITED STATES PATENT AND TRADEMARK OFFICE
CERTIFICATE OF CORRECTION

PATENT NO. : 9,717,619 B2
APPLICATION NO. : 14/352567
DATED : August 1, 2017
INVENTOR(S) : Boris Dodin Page 1 of 1

It is certified that error appears in the above-identified patent and that said Letters Patent is hereby corrected as shown below:

In the Claims

Column 10, Line 11: "hone" should be "bone"

Column 10, Line 20: "hone" should be "bone"

Column 10, Line 28: "hone" should be "bone"

Column 11, Line 33: "joint" should be "joints"

Signed and Sealed this
Twenty-eighth Day of November, 2017

Joseph Matal
*Performing the Functions and Duties of the*
*Under Secretary of Commerce for Intellectual Property and*
*Director of the United States Patent and Trademark Office*